United States Patent
Shirao et al.

[11] Patent Number: 5,223,865
[45] Date of Patent: Jun. 29, 1993

[54] METHOD AND APPARATUS FOR MEASURING VISUAL FUNCTION

[75] Inventors: Yutaka Shirao; Kazuo Kawasaki, both of Ishikawa; Toshiaki Mizuno, Gamagori; Kazuhiro Yoshimura; Yasuhisa Murakami, both of Toyohashi, all of Japan

[73] Assignee: Nidek Co., Ltd., Aichi, Japan

[21] Appl. No.: 691,896

[22] Filed: Apr. 26, 1991

[30] Foreign Application Priority Data

Apr. 28, 1990 [JP] Japan .................. 2-114450
Feb. 28, 1991 [JP] Japan .................. 3-057798

[51] Int. Cl.⁵ .............................. A61B 3/02
[52] U.S. Cl. .................. 351/243; 351/329; 351/240; 351/241
[58] Field of Search ......... 351/239, 240, 241, 243, 351/246

[56] References Cited

U.S. PATENT DOCUMENTS 3,623,799  11/1971  Millodot .
4,012,128  3/1977   Regan .
4,145,123  3/1979   Krahn .
4,511,228  4/1985   von Gierke et al. ............. 351/243
4,572,630  2/1986   Task et al. .

FOREIGN PATENT DOCUMENTS 3143949  9/1982  Fed. Rep. of Germany .

Primary Examiner—Rodney B. Bovernick
Assistant Examiner—Hung Xuan Dang
Attorney, Agent, or Firm—Nikaido, Marmelstein, Murray & Oram

[57] ABSTRACT

The inventive method and apparatus are based on the display of a striped target with constantly accurate contrast to the patient for finding a visual function disturbance associated with such eye diseases as glaucoma or diabetic repinopathy at their earlier stage. A sight target of striped pattern is formed on the screen having a uniform brightness, the striped target is oscillated in the direction orthogonal to the striped pattern while varying the contrast of striped target and showing it to the patient, and the threshold of the pattern contrast which can be recognized visually by the patient is measured.

20 Claims, 5 Drawing Sheets

METHOD AND APPARATUS FOR MEASURING VISUAL FUNCTION

BACKGROUND OF THE INVENTION

This invention relates to a method and apparatus for measuring visual function of an eye.

Perimetry have been a method of diagnosis for eye diseases such as glaucoma which, results in visual field disturbance. Perimetry is conducted in such a way that the coordinates are established so that the patient's eye is placed at or near the center of a sphere of a hemispherical projection screen and the visual field is measured while varying the stimulus point of a target which is projected on the screen. Although this method is useful for perimetry, it was reported that at the time when the emergence of visual field disturbance is revealed by perimetry, the patient has already lost half of optic nerve cells of the patient's eye. Therefore, it has been desired to detect the patient's symptom before the disease has advanced to this stage. It has also been desired against such diseases as diabetic repinopathy to find a symptom at their earlier stage for improving the results of screening.

SUMMARY OF THE INVENTION

A first object of this invention is to provide a method and apparatus for measuring the visual function of the patient's eye which are capable of detecting symptoms of eye disease such as glaucoma and diabetic repinopathy at their earlier stages.

A second object of this invention is to provide an apparatus for measuring the visual function accurately without being affected by the brightness of the examination environment and the light source.

In order to achieve the above first objective, the inventive method and apparatus for measuring the visual function are designed to form a target of a striped pattern on a screen of almost uniform brightness, oscillate the striped target in the direction orthogonal to the stripes while varying the contrast of the striped target, and measure the threshold of contrast which can be recognized visually by the patient. In consequence, it becomes possible to detect the visual function disturbance that could not have been done by the conventional method of perimetry.

Next, the principle of examination based on this invention will be explained.

The study on the visual function of the eye has revealed the presence of a longitudinal relation of the visual cells, bipolar cells and ganglion cells, and a lateral relation of the horizontal cells and amacrine cells. The longitudinal relation serves to convert the light which has reached a visual cell into an electrical signal and transmit image information to the brain through the visual cell. The lateral relation is made up of horizontal cells located between visual cells and bipolar cells and amacrine cells located between bipolar cells and ganglion cells, and it has the roles of the enhancement of contrast, sense of moving objects and stereopsis. The lateral relation enables the human's eye to see an object accurately under illumination conditions which extend as wide as $1-10^{11}$, and also sense a small spot and dirt on a white wall.

It is known that a oscillatory potential wave which relates to the lateral function becomes abnormal at the very early stage of diabetic retinopathy. By paying attention to the fact that the emergence of a defective lateral function is inferred at the early stage of a visual field disturbance, the present invention is intended to detect the patient's symptom of visual function based on the correspondence to the lateral function. Specifically, a pattern of stripes with a proper interval (such a span as one horizontal cell link, i.e., about 200 $\mu$m on the retina, is appropriate) is focused on the retina, and the retina is stimulated by oscillating the pattern. The amplitude of oscillation is selected to be a half or more of the width of a stripe, and the oscillation frequency is selected within the range of having no influence on the static detection ability for the easiness of detection (a setting to 4 Hz in the observing distance of 300 mm allows easy setting of the threshold which will be explained later). The examination is conducted to find the lower limit of contrast at which the patient can recognize the movement (swing) of the striped pattern that is projected on the center of adaptation field. In case horizontal cells and amacrine cells are normal, the patient can recognize the movement at a low contrast below the threshold which is set to the border between normal eyes and abnormal eyes. If these cells do not function normally, the patient cannot recognize the movement of a low contrast striped pattern.

The above-mentioned second objective is achieved through the calibration of the striped target on the screen.

DESCRIPTION OF THE PREFERRED EMBODIMENT

Figure 1:
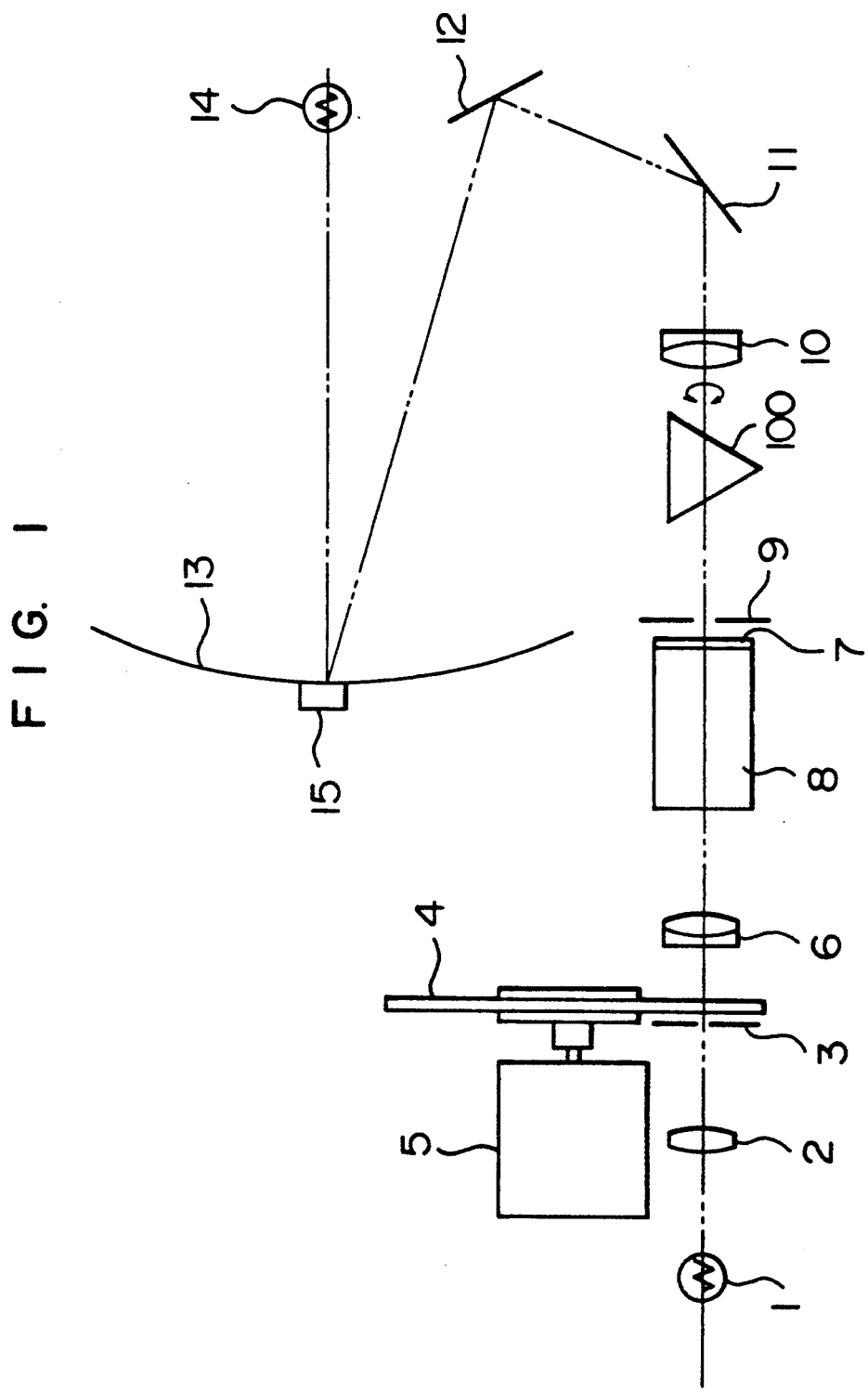
FIG. 1 is a diagram showing the optical system of the measuring apparatus based on an embodiment of this invention.

FIG. 1 is a diagram showing the disposition of the optical system in the measuring apparatus based on an embodiment of this invention. In the figure, reference numeral 1 denotes a halogen lamp which serves as a second light source, and the light illuminated by the halogen lamp 1 is incident to a disc 4 by way of a condenser lens 2 and an aperture 3. The disc 4 has a formation of a wedge-type filter which varies the transmittance on the light projection path continuously by being rotated by a pulse motor 5. The transmittance of the light path may be varied in steps by combining several filters, instead of being varied continuously. This embodiment is designed to vary the transmittance in steps so that the system has 200-step resolutions in the contrast of the striped target ranging 0.1–10%.

Figure 2:
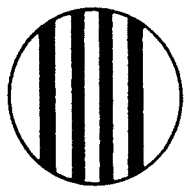
FIG. 2 is a diagram used to explain the striped target.

The light which has passed the filter of the disc 4 illuminates a transparent grating 7 virtually uniformly through a projection lens 6. The transparent grating 7 has a print of a striped pattern made up of bright sections with a transmittance of 80% or more and dark sections with a transmittance of 0%. The bright sections transmit the light from the light source 1 and the dark sections interrupt the light. The transparent grating 7 is designed so that the striped target (see FIG. 2) projected on the screen 13 is viewed by the patient's eye at a visual angle of 5° and a stripe pitch of 0.5°. A photosensor 15 is disposed in the center of the projected striped target on the screen 13. The patient recognizes the striped target in the center of visual field when the patient fixedly matches the photosensor 15 in the center of the screen 13.

The transparent grating 7 is oscillated in the direction orthogonal to the stripes at a frequency of 4 Hz and an amplitude of 0.25° by means of a transparent grating driver 8. The transparent grating driver 8 of this embodiment is a simple mechanism to accomplish the small amplitude of oscillation, as follows. The mechanism includes an oscillation shaft, with its one end fixed to the transparent grating 7 and another end fixed to the shaft of a pulse motor, and it oscillates the transparent grating 7 by being driven through the reciprocal rotations of the pulse motor.

A projection lens 10 focuses the image of the transparent grating 7 on a screen 13 at its center through a diaphragm 9 and such a light conduction means as mirrors 11 and 12. The screen 13 has a shape of hemisphere and a setting of screen size of 20° and an observing distance of 300 mm from the patient's eye. The front of the screen 13 is covered so as to shut out the external light, and the patient is instructed to look at the striped target which is projected on the screen 13 with his right or left eye through an aperture formed at the center of the screen.

Reference numeral 14 denotes a pair of halogen lamps as a first light source located on the right and left of the aperture, and these lamps illuminate the screen 13 evenly. The screen 13 has a background luminance of 500 cd/cm$^2$, which is equal to the brightness of the back sections of the striped target, and the striped target is designed to have the maximum brightness of its bright sections brighter by about 10% than the dark sections by means of the disc 4.

Reference numeral 15 denotes a photosensor, which detects a change in the luminance due to the influence of an extraneous light or the aging of the light source with the intention of maintaining the accurate contrast of the striped target. The photosensor 15 is also used as a fixation target for preventing the induction of movement of the patient's eye. The photosensor 15 has a light input window which is dimensioned to be preferably a half or less of the stripe pitch for simplifying the process, although this is not an indispensable condition.

Next, the principal portion of the electrical drive system will be explained separately for its calibration mechanism to maintain the accurate contrast and eye examination mechanism.

Figure 3:
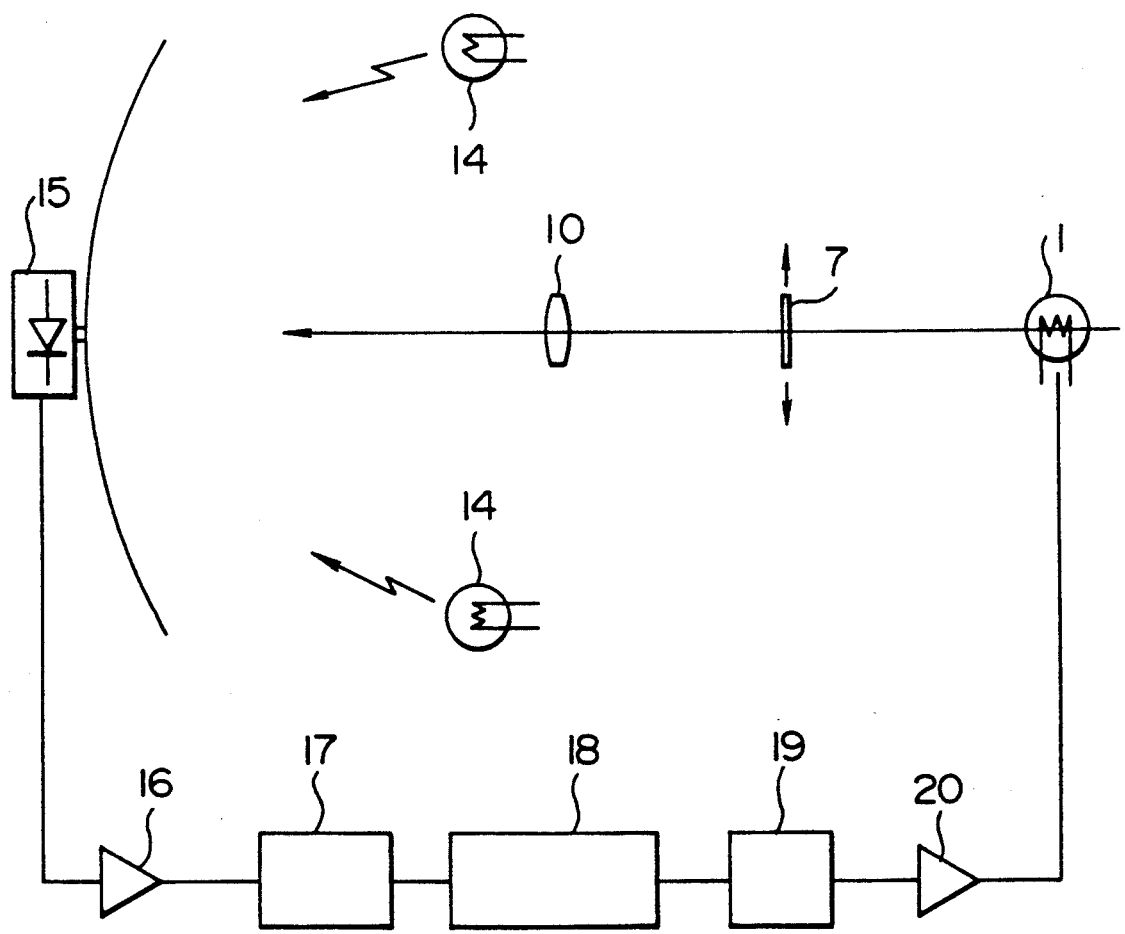
FIG. 3 is a block diagram showing the electrical system of the calibration mechanism.

FIG. 3 is a block diagram of the electrical system of the calibration mechanism. The transparent grating driver 8 moves the transparent grating 7 so that its bright section and dark section are projected alternately, and the luminance (quantity of light) is measured at each projection. The light incident on the photosensor 15 is converted into an electrical signal, and it is amplified on the amplifier 16. The amplified signal is converted into digital data by an A/D converter 17, and the data is input to a microcomputer 18. The microcomputer 18, which also controls the overall apparatus, calculates the contrast of the projected stripe pattern from the luminance values of the bright section and dark section in accordance with the following formula.

$$\text{Contrast (\%)} = \frac{A - B}{A + B} \times 100 \text{ (\%)}$$

where A is the luminance of the bright section of the stripe pattern, and B is the luminance of the dark section (luminance of adaptation field).

The microcomputer 18 operates as a light adjustment means to compare the calculated contrast with the prescribed value and operate on a PWM pulse generator 19 to produce pulse signal so that the halogen lamp 1 produces an increased light output or decreased light output when the calculated luminance is lower than or higher than the prescribed value, respectively. A lamp driver 20 controls the application voltage to the halogen lamp 1 in accordance with the pulse signal.

Figure 4:
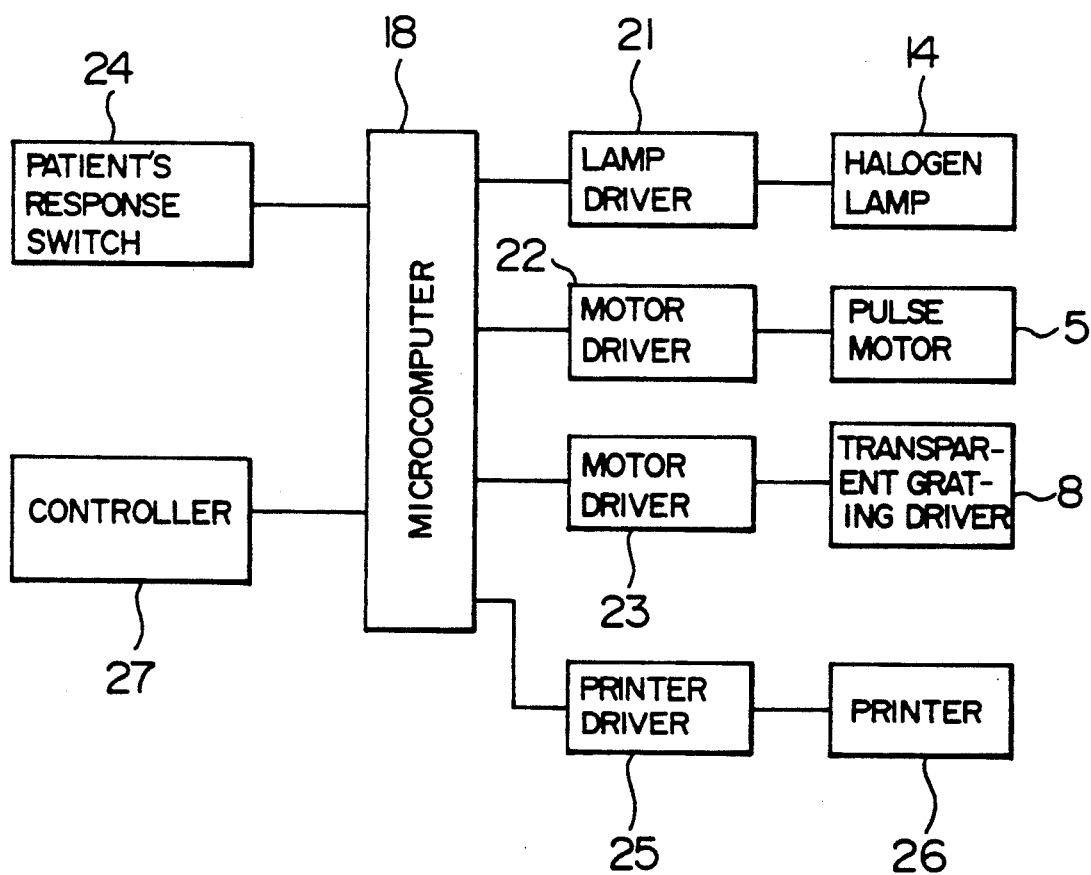
FIG. 4 is a block diagram showing the electrical system for controlling the operation in carrying out the examination of an eye.

FIG. 4 is a block diagram of the electrical system for controlling the operation of eye examination (The illumination circuit of the halogen lamp 1, which is shown in FIG. 3, is not shown in FIG. 4).

The microcomputer 18 operates as a control means to control the switching operation of the halogen lamp 14 through a lamp driver 21, control the drive of the pulse motor 5 through a motor driver 22, and control the transparent grating driver 8 through a motor driver 23. A response switch 24 which is operated by the patient produces a signal and it is input to the microcomputer 18. Indicated by 26 is a printer for printing the result of examination, and 25 is a printer driver. 27 is a controller which specifies the contrast and the speed of pointing.

The operation of the apparatus of this embodiment arranged as described above will be explained with reference to the flowcharts.

Figure 5:
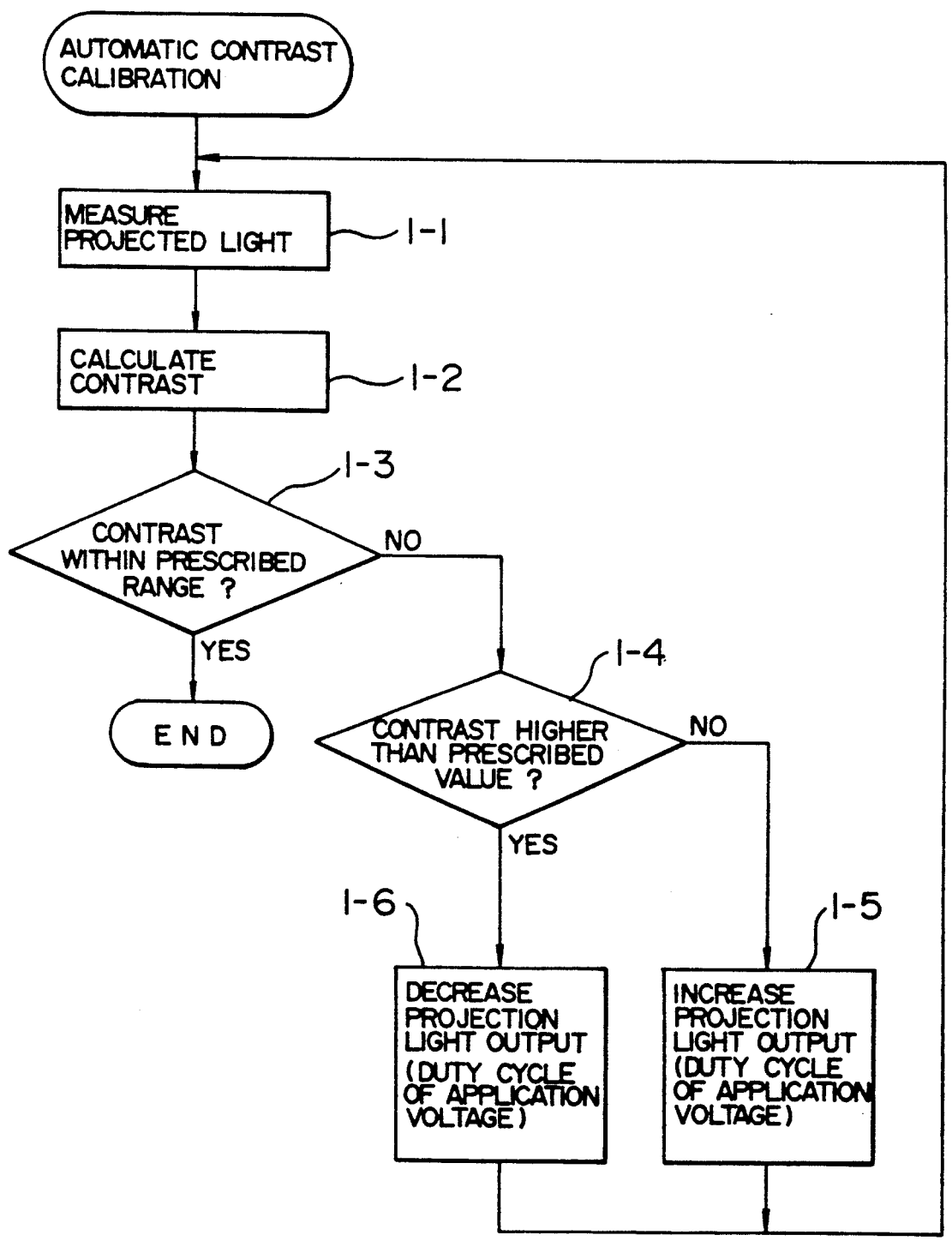
FIG. 5 is a flowchart of contrast calibration.

FIG. 5 is a flowchart showing the operation of contrast calibration.

When the power switch (not shown) of the apparatus is turned on, the halogen lamps 1 and 14 light up and the disc 4 is set to its initial position by the operation of the pulse motor 5. The transparent grating driver 8 moves the transparent grating 7 so that the bright section and dark section of the striped target are projected alternately on to the light input window, and the quantity of the projected light is measured at each projection (step 1-1). The contrast is calculated from the measured quantity of projected light (step 1-2), and the calculated value is compared with the prescribed value (step 1-3). If the difference of these values is within the predetermined range, the calibrating operation completes. If the difference is in excess of the prescribed range, it is discriminated with respect to the prescribed value (step 1-4), and the application voltage to the halogen lamp 1 is increased or decreased by predetermined steps (step 1-5 or 1-6). These operations are repeated until the difference of contrast from the prescribed value enters the predetermined range.

Figure 6:
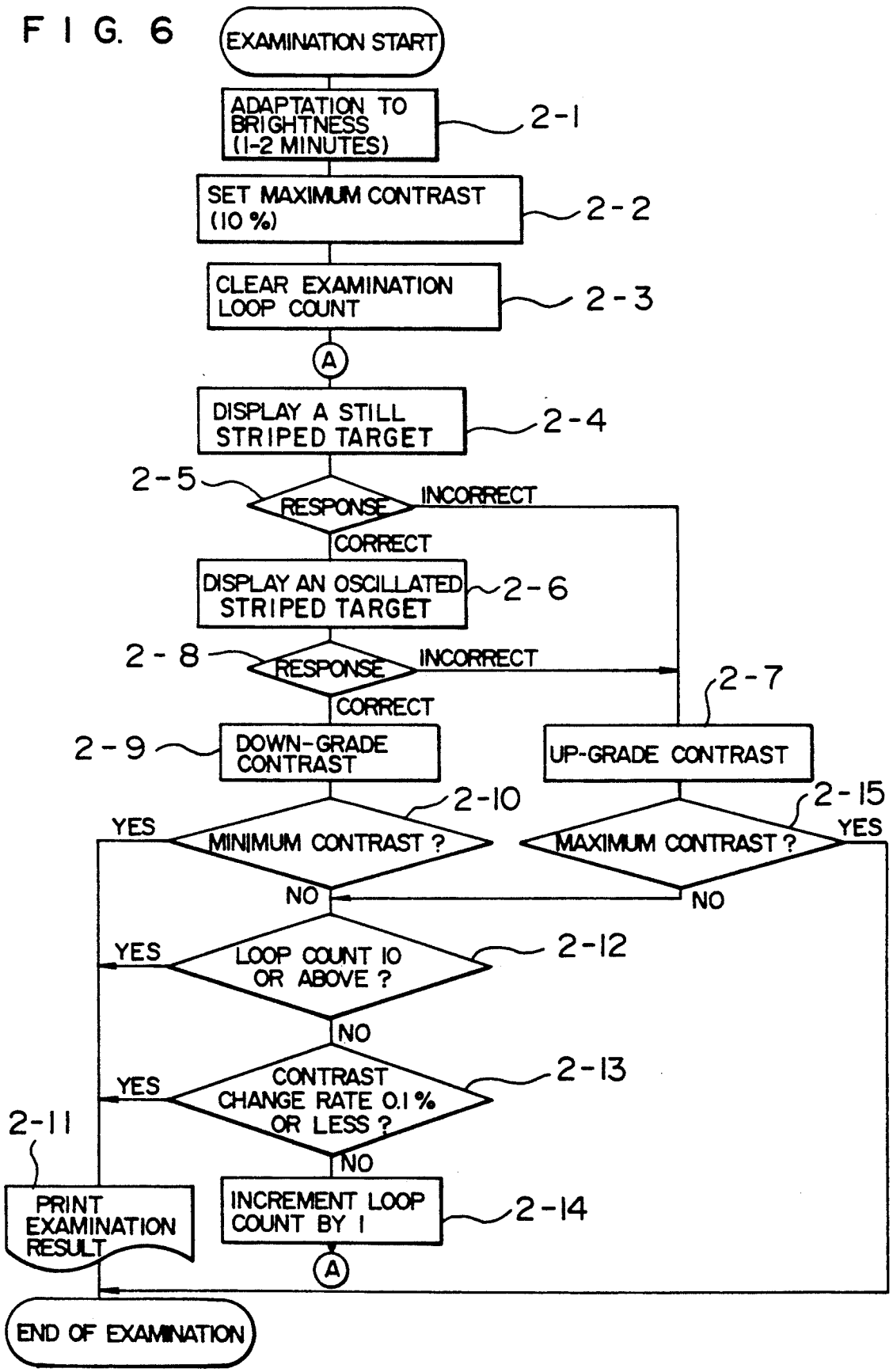
FIG. 6 is a flowchart of examination.

FIG. 6 is a flowchart showing the examination operation. At the beginning of the examination, the patient is instructed to look at the screen for one to two minutes (step 2-1) so that the eye to be examined is adapted to the brightness. Next, the disc 4 is rotated, with the contrast of striped target being set to 10% (step 2-2), and the examination loop count is initialized to zero (step 2-3). One loop is a series of examination conducted at a certain contrast setting.

On completion of this step, the inspector depresses the start key of the controller 27, and thereafter the measurement takes place automatically. Although the contrast of the striped target can be set freely, in this embodiment a still striped target is pointed (step 2-4), and the patient is asked whether he (or she) can recognize the striped target with the eye to be examined under test (step 2-5). If the patient has made a correct response, the examination sequence proceeds to step 2-6, or otherwise proceeds to step 2-7.

In step 2-6, the transparent grating 7 is oscillated, and the patient is asked to respond in this situation (step 2-8). If the patient has recognized the oscillating striped target correctly, the examination sequence proceeds to step 2-9, or otherwise proceeds to step 2-7.

In step 2-9, the contrast of striped target is lowered by one step. If the new contrast is the lowest contrast as discriminated in step 2-10, the examination sequence proceeds to step 2-11. In case the contrast is not the lowest, it is tested whether or not the examination loop count is ten or above (step 2-12). If the loop count is ten or above, the examination sequence proceeds to step 2-11 thereby to print the examination result.

If the loop count is less than ten, it is tested whether or not the width of contrast change is 0.1% or less (step 2-13). If the width of change is 0.1% or less, in which case the examination result is determined to be accurate, the examination sequence proceeds to step 2-11, otherwise the loop count is incremented by one and the sequence proceeds to the node A (step 2-14).

In step 2-7, the contrast is raised by a half step, and if it is not the maximum value as discriminated in step 2-15, the sequence proceeds to step 2-12.

In step 2-11, the examination result is printed out. The examination result eye is determined to be normal when the contrast is 1% or less, or otherwise is determined to be abnormal, based on the clinical convention.

The foregoing examination is based on the measurement in automatic mode, and it is also possible to allow the examination to set the contrast value and other parameters. Moreover, this examination method can have enhanced accuracy by conducting the measurement several times while changing the direction of stripes, and averaging the measured values. The direction of the stripes is changed by an image rotator 100 disposed on the screen side of the transparent grating 7.

Although in the foregoing embodiment, the contrast is switched by replacing the disc 4 which is disposed in the striped target projection optical system, it can also be implemented by adjusting the light output of the projection light source. The light output of the halogen lamp 14 may be adjusted for the calibration of contrast, instead of the adjustment of the light output of the halogen lamp 1, or control data of the disc 4 may be converted. In addition to the disclosed preferred embodiments, the term "screen" as used herein, includes TV monitors, etc. Accordingly, various changes and modifications can be made for this embodiment, and these variants ar included in the present invention within the range of its unique technical thought.

According to this invention, it becomes possible to find a view field failure of glaucoma and the early-stage symptom of diabetic retinopathy.

In addition, it becomes possible to implement the accurate examination which is free from the influences of the examination environment and the aging of the light source.

We claim:

1. An apparatus for measuring a visual function by measuring a threshold of contrast of a striped target whose swing can be recognized visually by a person under examination, said apparatus comprising:
   a screen having a virtually uniform brightness;
   striped target forming means for forming the striped target on said screen;
   contrast varying means for varying a contrast of the striped target; and
   striped target oscillating means for oscillating the striped target without inducing movement of an eye of the person under examination in a direction virtually orthogonal to a stripe pattern on the striped target.

2. An apparatus according to claim 1, wherein said screen has a hemispherical shape.

3. An apparatus according to claim 1, wherein said contrast varying means varies a quantity of light which is projected by a first light source on to said screen.

4. An apparatus according to claim 1, wherein said striped target forming means comprises:
   a light source;
   a transparent grating having light transmissive sections which transmit light from said light source and light interruptive sections which interrupt the light from said light source, with said light transmissive sections and light interruptive sections being arranged in stripes; and
   means for delivering the light, which has passed through said transparent grating, to said screen.

5. An apparatus according to claim 4, wherein said contrast varying means comprises a filter or combination of filters which varies transmittance of the light emitted by said light source.

6. An apparatus according to claim 4, wherein said striped target oscillating means comprises an oscillation mechanism which is linked to said transparent grating and adapted to oscillate said grating in the direction virtually orthogonal to the stripe pattern.

7. An apparatus according to claim 1, wherein the oscillation of the striped target has an amplitude which is about a half of the stripe pattern.

8. An apparatus according to claim 1, wherein the frequency of oscillation of the striped target is 4 Hz for a distance of 300 mm between the striped target projected on said screen and the eye of the person to be measured.

9. An apparatus according to claim 1 further comprising:
   control means for controlling variation of contrast and oscillation of the striped target; and
   an interface between said control means and the person under examination,
   said control means varying the contrast of stripe pattern in a state of halted oscillation of the striped target or in a state of oscillation of the striped target depending on a first signal received through said interface indicative of whether or not the person under examination has recognized visually the contrast of striped target.

10. An apparatus according to claim 9 further comprising means of determining a threshold of the contrast of striped target which can be recognized visually by the person under examination based on said first signal and variation of contrast.

11. An apparatus according to claim 10 further comprising means for outputting the determined threshold.

12. An apparatus according to claim 1 further comprising calibrating means for calibrating the contrast of the striped target formed on said screen.

13. An apparatus according to claim 12, wherein said calibrating means for producing a second signal which represents a quantity of light on said screen; and means for adjusting the light output of at least one of said screen and a light source in response to said second signal.

14. An apparatus according to claim 13, wherein a light detection means is disposed at virtually a center of said screen where the striped target is formed and is used as a fixation target.

15. An apparatus according to claim 14, wherein said light detection means has a light input window which is smaller in width than widths of bright sections and dark sections of the striped target and operates to detect quantities of light at the bright sections and dark sections when each section comes to cover said light input window by the oscillation of the striped target.

16. An apparatus according to claim 1 further comprising means of varying direction of the stripe pattern of the striped target.

17. A method of measuring a visual function by measuring a threshold of a contrast of a striped target whose swing can be recognized visually by a person under examination, said method comprising the steps of:

maintaining a virtually uniform brightness of a screen;

forming the striped target on said screen;

varying a contrast of the striped target;

oscillating the striped target without inducing movement of an eye of the person under examination in a direction virtually orthogonal to a stripe pattern of the striped target;

letting the person under examination recognize visually the striped target; and evaluating the threshold of contrast of the striped target based on a response of visual recognition made by the person.

18. A method according to claim 17 further comprising a step of varying a direction of the stripe pattern of the striped target.

19. An apparatus for measuring a visual function by measuring a threshold of a contrast of a striped target whose swing is recognized visually by a person under examination, said apparatus comprising:

a screen having a virtually uniform brightness;

means for forming the striped target on said screen;

means for varying the contrast of the striped target; and means for oscillating the striped target with a speed which an eye of the person under examination follows in a direction virtually orthogonal to a stripe pattern of the striped target.

20. An apparatus for measuring a visual function by measuring a threshold of a contrast of a striped target whose swing is recognized visually by a person under examination, said apparatus comprising:

a screen having a virtually uniform brightness;

means for forming the striped target on said screen;

means for varying the contrast of the striped target; and means for oscillating the striped target with a frequency which an eye of the person under examination follows in a direction virtually orthogonal to a stripe pattern of the striped target.

* * * * *